1

United States Patent
Cooke et al.

(10) Patent No.: US 6,630,495 B1
(45) Date of Patent: Oct. 7, 2003

(54) FUNGICIDES

(75) Inventors: Tracey Cooke, St. Albans (GB); Tennyson Ekwuru, Lyon Cedex (FR); David Hardy, Cambridge (GB); Peter Millward, Cambridge (GB); Brian Moloney, Oxon (GB); Andrew Pettinger, Lyons (FR); Peter Stanley Thomas, Cambridge (GB); Richard Michael Turner, Cambridge (GB)

(73) Assignee: Bayer Cropscience GmbH (DE)

( * ) Notice: Subject to any disclaimer, the term of this patent is extended or adjusted under 35 U.S.C. 154(b) by 0 days.

(21) Appl. No.: 10/049,981

(22) PCT Filed: Aug. 11, 2000

(86) PCT No.: PCT/EP00/08269

§ 371 (c)(1),
(2), (4) Date: Jul. 22, 2002

(87) PCT Pub. No.: WO01/11966

PCT Pub. Date: Feb. 22, 2001

(30) Foreign Application Priority Data

Aug. 18, 1999 (GB) .............................. 9919588

(51) Int. Cl.$^7$ ........................ C07D 213/02; A01N 43/40
(52) U.S. Cl. ........................ 514/357; 546/330; 546/334; 546/336; 546/337
(58) Field of Search ................. 546/330, 334, 546/336, 337; 514/357

(56) References Cited

U.S. PATENT DOCUMENTS

| 3,609,158 A | 9/1971 | Torba ........................ 546/302 |
| 4,423,222 A | 12/1983 | Ash et al. ................... 548/163 |

FOREIGN PATENT DOCUMENTS

| EP | 0329020 | 8/1989 |
| EP | 0334138 | 9/1989 |
| EP | 0404190 | 12/1990 |
| EP | 0726266 | 8/1996 |
| JP | 64-003162 | 1/1989 |
| JP | 07-173139 | 7/1995 |
| JP | 08-208615 | 8/1996 |
| WO | 97/08135 | 3/1997 |
| WO | 99/07687 | 2/1999 |
| WO | 99/42447 | 8/1999 |

OTHER PUBLICATIONS

O'Brien et al, J. Med. Chem, vol. 37, pp. 1810–1822, 1994.*

* cited by examiner

*Primary Examiner*—Zinna Northington Davis
(74) *Attorney, Agent, or Firm*—Ostrolenk, Faber, Gerb & Soffen, LLP

(57) ABSTRACT

Compounds of formula (I) or (II):

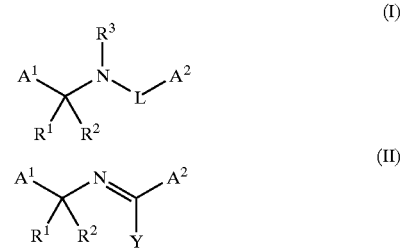

or salts therefor are used as phytopathogenic fungicides wherein the various radicals and substitutents are as defined in the description. Pesticidal compositions contain these compounds together with an agriculturally acceptable diluent or carrier. The compounds and compositions are applied in methods for combating pests.

3 Claims, No Drawings

FUNGICIDES

This application is a 371 of PCT/EP00/08269 filed Aug. 1, 2000.

This invention relates to compounds having fungicidal activity.

In a first aspect the invention provides the use of compounds of general formula I or II or salts thereof as phytopathogenic fungicides

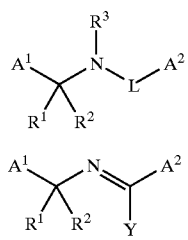

wherein
- $A^1$ is 2-pyridyl or its N-oxide, each of which may be substituted by up to four groups at least one of which is haloalkyl;
- $A^2$ is heterocyclyl or carbocyclyl, each of which may be substituted ($A^2$ is preferably optionally substituted heterocyclyl or optionally substituted phenyl);
- $R^1$ and $R^2$, which may be the same or different, are $R^b$, cyano, nitro, halogen, —$OR^b$, —$SR^b$ or optionally substituted amino, or $R^1$ and $R^2$ together with the carbon to which they are attached may form a 3-, 4-, 5- or 6-carbo- or heterocyclic ring, which may be substituted ($R^1$ and $R^2$ are preferably hydrogen, acyl, optionally substituted alkyl or cyano);
- $R^3$ is $R^b$, —$OR^b$, or —$N(R^b)_2$, cyano, N-substituted iminomethyl or nitro; or $R^3$ and $A^2$, together with the interconnecting atoms, may form a 5- or 6-membered ring ($R^3$ is preferably hydrogen, N-substituted iminomethyl or optionally substituted alkyl);
- L is —C(=X)— or —$S_2$—, where X is oxygen, sulfur, N—$OR^b$, N—$R^b$ or N—$N(R^b)_2$ (L is preferably —C(=O)—, —C(=S)— or —C(=$NOR^b$)—); and
- Y is halogen, —$OR^b$, —$SR^b$, —$N(R^b)_2$, —$NR^b(OR^b)$ or —$NR^bN(R^b)_2$ (preferably —$OR^b$, —$SR^b$ or —$N(R^b)_2$);
- and $R^b$, which may be the same or different, is alkyl, alkenyl, alkynyl, carbocyclyl or heterocyclyl, each of which may be substituted; or hydrogen or acyl, or two adjacent $R^b$ groups together with the interconnecting atoms, may form a 5- or 6-membered ring;
- with the proviso that when $A^1$ is 2-pyridyl, $R^1$ is hydrogen, $R^2$ is hydrogen, optionally substituted alkyl or acyl, L is —C(=X)— or —$SO_2$—, X is oxygen or sulfur and $R^3$ is hydrogen or optionally substituted alkyl, $A^2$ is not optionally substituted phenyl.

Preferred substituents on the 2-pyridyl group ($A^1$) are halogen, hydroxy, cyano, nitro, $SF_5$, trialkylsilyl, optionally substituted amino, acyl, or a group —$R^a$, —$OR^a$ or —$SR^a$, or a group —C($R^a$)=N—Q, where Q is —$R^a$, —$OR^a$, —$SR^a$ or optionally substituted amino, wherein $R^a$ is alkyl, alkenyl, alkynyl, carbocyclyl or heterocyclyl, each of which may be substituted; or two adjacent substituents together with the atoms to which they are attached form an optionally substituted ring which can contain up to 3 hetero atoms. Especially preferred substituents are alkoxy, alkyl, cyano, halogen, nitro, alkoxycarbonyl, alkylsulfinyl, alkylsulfonyl and trifluoromethyl, particularly chlorine and trifluoromethyl.

Preferably, the 2-pyridyl group is substituted at the 3 and/or 5 position.

The invention also includes any of the compounds specifically exemplified hereinafter.

Any alkyl group may be straight or branched and is preferably of 1 to 10 carbon atoms. especially 1 to 7 and particularly 1 to 5 carbon atoms.

Any alkenyl or alkynyl group may be straight or branched and is preferably of 2 to 7 carbon atoms and may contain up to 3 double or triple bonds which may be conjugated, for example vinyl, allyl, butadienvl or propargyl.

Any carbocyclyl group may be saturated, unsaturated or aromatic, and contain 3 to 8 ring-atoms. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocylic should be similarly construed. In addition, the term carbocyclyl includes any fused combination of carbocyclyl groups, for example naphthyl, phenanthryl, indanyl and indenyl.

Any heterocyclyl group may be saturated, unsaturated or aromatic, and contain 5 to 7 ring-atoms up to 4 of which may be hetero-atoms such as nitrogen, oxygen and sulfur, Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazoiinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Any alkyl, alkenyl, alkynyl, carbocyclyl or heterocyclyl group, when substituted, may be substituted by one or more substituents, which may be the same or different, and may be selected from the list: hydroxyl; mercapto; azido; nitro; halogen: cyano; acyl; optionally substituted amino; optionally substituted carbocyclyl; optionally substituted heterocyclyl; cvanato; thiocyanato; —$SF_5$; —$OR^a$; —$SR^a$ and —$Si(R^a)_3$, where $R^a$ is alkyl, alkenyl, alkvnyl, carbocyclyl or heterocyclyl, each of which may be substituted. In the case of any carbocyclyl or heterocyclyl group the list includes additionally: alkyl, alkenyl and alkynyl, each of which may be substituted. Preferred substituents on any alkyl, alkenyl or alkynyl group are alkoxy, haloalkoxy or alkylthio, each containing 1 to 5 carbon atoms; halogen; or optionally substituted phenyl. Preferred substituents on any carbocyclyl or heterocyclyl group are alkyl, haloalkyl, alkoxy, haloalkoxy or alkylthio, each containing 1 to 5 carbon atoms; halogen; or optionally substituted phenyl.

In the case of any alkyl group or any unsaturated ring-carbon in any carbocycyl or heterocyclyl group the list includes a divalent group such as oxo or imino, which may be substituted by optionally substituted amino, $R^a$ or —$OR^a$. Preferred groups are oxo, imino, alkylimino, oximino, alkyloximino or hydrazono.

Any amino group, when substituted and where appropriate, may be substituted by one or two substituents which may be the same or different, selected from the list:

optionally substituted alkyl, optionally substituted amino, —OR$^a$ and acyl groups. Alternatively two substituents together with the nitrogen to which they are attached may form a heterocyclyl group, preferably a 5 to 7-membered heterocyclyl group, which may be substituted and may contain other hetero atoms, for example morpholino, thiomorpholino or piperidinyl.

The term acyl includes the residues of sulfur and phosphorus-containing acids as well as carboxylic acids. Typically the residues are covered by the general formulae —C(=X$^a$)R$^c$, —S(O)$_p$R$^c$ and —P(=X$^a$)(OR$^a$)(OR$^a$), where appropriate X$^a$ is O or S, R$^c$ is as defined for R$^a$, —OR$^a$, —SR$^a$, optionally substituted amino or acyl; and p is 1 or 2. Preferred groups are —C(=O)R$^d$, —C(=S)R$^d$, and —S(O)$_p$R$^d$ where R$^d$ is alkyl, $C_1$ to $C_5$ alkoxy, $C_1$ to $C_5$ alkylthio, phenyl, heterocyclyl or amino, each of which may be substituted.

Complexes of compounds of the invention are usually formed from a salt of formula MAn$_2$, in which M is a divalent metal cation, e.g. copper, manganese, cobalt, nickel, iron or zinc and An is an anion, e.g. chloride, nitrate or sulfate.

In cases where the compounds of the invention exist as the E and Z isomers, the invention includes individual isomers as well as mixtures thereof.

In cases where compounds of the invention exist as tautomeric isomers, the invention includes individual tautomers as well as mixtures thereof.

In cases where the compounds of the invention exist as optical isomers, the invention includes individual isomers as well as mixtures thereof.

The compounds of the invention have activity as fungicides, especially against fungal diseases of plants, e.g. mildews and particularly cereal powdery mildew (*Erysiphe graminis*) and vine downy mildew (*Plasmopara viticola*), rice blast (*Pyricularia orvzae*), cereal eyespot (*Pseudocercosporella herpotrichoides*), rice sheath blight (*Pellicularia sasakii*), grey mould (*Botrvtis cinerea*), damping off (*Rhizoctonia solani*), wheat brown rust (*Puccinia recondita*), late tomato or potato blight (*Phytophihora infestans*), apple scab (*Venturia inaequalis*), and glume blotch (*Leptosphaeria nodorum*). Other fungi against which the compounds may be active include other powdery mildews, other rusts, and other general pathogens of Deuteromycete, Ascomycete, Phycomycete and Basidomycete origin.

The invention thus also provides a method of combating fungi at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition, the composition can comprise one or more additional active ingredients, for example compounds known to possess plant-growth regulant, herbicidal, fungicidal, insecticidal, acaricidal, antimicrobial or antibacterial properties. Alternatively the compound of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxvlate, for example a metal carboxvlate of a long chain fatty acid; an N-acylsarcosinate; mono- or di-esters of phosphoric acid with fatty alcohol ethoxylates or alkyl phenol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl-aryl sulfonates such as alkyl-benzene sulfonates or lower alkylnaphthalene sulfonates, e.g. butyl-naphthalene sulfonate; salts of sulfonated naphthalene-formaldehyde condensates; salts of sulfonated phenol-formaldehyde condensates; or more complex sulfonates such as the amide sulfonates, e.g. the sulfonated condensation product of oleic acid and N-methyl taurine; the dialkyl sulfosuccinates, e.g. the sodium sulfonate of dioctyl succinate; acid derivatives of alkyl glycosides and alkylpolyglycosides materials and their metal salts, e.g. alkyl polyglycoside citrate or tartrate materials; or mono-, di- and tri-alkyl esters of citric acid and their metal salts.

Nonionic agents include condensation products of fatty acid esters, fatty alcohols, fatty acid amides or fatty-alkyl- or alkenyl-substituted phenols with ethylene and/or propylene oxide; fatty esters of polyhydric alcohol ethers, e.g. sorbitan fatty acid esters; condensation products of such esters with ethylene oxide, e.g. polyoxyethylene sorbitan fatty acid esters; alkyl glycosides, alkyl polyglycoside materials; block copolymers of ethylene oxide and propylene oxide; acetylenic glycols such as 2,4,7,9-tetramethyl-5-decyne-4,7-diol, ethoxylated acetylenic glycols; acrylic based graft copolymers; alkoxylated siloxane surfactants; or imidazoline type surfactants, e.g. 1-hydroxyethyl-2-alkylimidazoline.

Examples of a cationic surface-active agent include, for instance, an aliphatic mono-, di-, or polyamine as an acetate, naphthenate or oleate; an oxygen-containing amine such as an amine oxide, polyoxyethylene alkylamine or polyoxypropylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, an aerosol, a dispersion, an aqueous emulsion, a microemulsion, a dispersible concentrate, a dusting powder, a seed dressing, a fumigant, a smoke, a dispersible powder, an emulsifiable concentrate, granules or an impregnated strip. Moreover it can be in a suitable form for direct application or as a concentrate or primary composition which requires dilution with a suitable quantity of water or other diluent before application.

A dispersible concentrate comprises a compound of the invention dissolved in one or more water miscible or semi-water miscible solvents together with one or more surface active and/or polymeric material. Addition of the formulation to water results in the crystalisation of the active ingredient, the process being controlled by the surfactants and/or polymers resulting in a fine dispersion.

A dusting powder comprises a compound of the invention intimately mixed and ground with a solid pulverulent diluent, for example, kaolin.

An emulsifiable concentrate comprises a compouid of the invention dissolved in a water-immiscible solvent which forms an emulsion or microemulsion on addition to water in the presence of an emulsifving agent.

A granular solid comprises a compound of the invention associated with similar diluents to those that may be employed in dusting powders, but the mixture is granulated by known methods. Alternatively it comprises the active ingredient absorbed or coated on a pre-formed granular carrier, for example, Fuller's earth, anapulgite, silica or limestone grit.

Wettable powders, granules or grains usually comprise the active ingredient in admixture with suitable surfactants and an inert powder diluent such as clay or diatomaceous earth, Another suitable concentrate is a flowable suspension concentrate which is formed by grinding the compound with water or other liquid, surfactants and a suspending agent.

The concentration of the active ingredient in the composition of the present invention, as applied to plants is preferably within the range of 0.0001 to 1.0 per cent by weight, especially 0.0001 to 0.01 per cent by weight. In a primary composition, the amount of active ingredient can vary widely and can be, for example, from 5 to 95 per cent by weight of the composition.

The invention is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds, A suitable application rate is within the range of from 5 to 1000 g per hectare, more preferably from 10 to 500 g per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the eariv stages of plant growth, as this is the time when the plant can be most severely damaged. The spray or dust can convenientlv contain a pre- or post-emergence herbicide if this is thought necessary. Sometimes, it is practicable to treat the roots, bulbs, tubers or other vegetative propagule of a plant before or during planting, for example, by dipping the roots in a suitable liquid or solid composition. When the active compound is applied directiv to the plant a suitable rate of application is from 0.025 to 5 kg per hectare, preferably from 0.05 to 1 kg per hectare.

In addition, the compounds of the invention can be applied to harvested fruits, vegetables or seeds to prevent infection during storage.

In addition, the compounds of the invention can be applied to plants or parts thereof which have been genetically modified to exhibit a trait such as fungal and/or herbicidal resistance.

In addition the compounds of the invention can be used to treat fungal infestations in timber and in public health applications. Also the compounds of the invention can be used to treat insect and fungus infestations in domestic and farm animals.

Compounds of the invention may be prepared, in known manner, in a variety of ways.

Compounds of formula Ia, i.e. compounds of general formula I where L is $L^1$ which is —C(=O)—, —C(=S)—, —SO$_2$— or —C(=NOH)— may be prepared according to reaction scheme 1 by reacting compounds of formula III or their hydrochloride salt with compounds of formula IV, where Q is a leaving group such as halogen, preferably chlorine. A preferred base is triethylamine.

Scheme 1

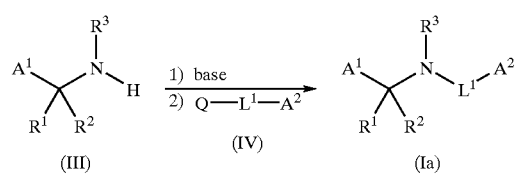

Compounds of formula IV where L1 is —C(=O)—, —C(=S)— or —SO$_2$— can be prepared from the corresponding hydroxy compound by methods known to the skilled chemist.

Compounds of formula IV can be isolated and used according to scheme 1. Alternatively, IV may be gene-rated in situ by methods, known to the skilled chemist, for example, using POCl$_3$ to gene-rate the acid chloride from the corresponding carboxylic acid, followed by addition of III.

Compounds of formula IVa, i.e. compounds of general formula IV where $L^1$ is —C(=NOH)— can be prepared according to reaction scheme 2.

Scheme 2

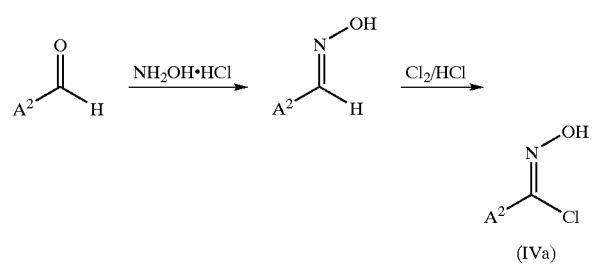

Compounds of formula Ib, i.e. compounds of general formula I where L is —C(=O)— may be prepared according to reaction scheme 3 by reacting compounds of formula III in the presence of a suitable base such as triethylamine with compounds of formula V in the presence of carbonyl diimidazole (CDI).

Scheme 3

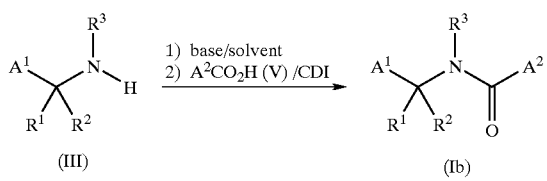

The preparation of compounds of formula V where $A^2$ is 3-hydroxy-2-benzo[b]furyl form part of the state of the art see P C Unangst, D T Connor, S R Miller, *J.Het.Chem.* 1996, 33, 2025–2030.

Many compounds of formula III may be prepared by methods described in international application PCT/GB/99/00304. Compounds of formula IIIa, i.e. compounds of general formula III where $R^1$ is hydrogen and $R^2$ is cyano, may be prepared by methods analogous to those described therein (see reaction scheme 3a).

Scheme 3a

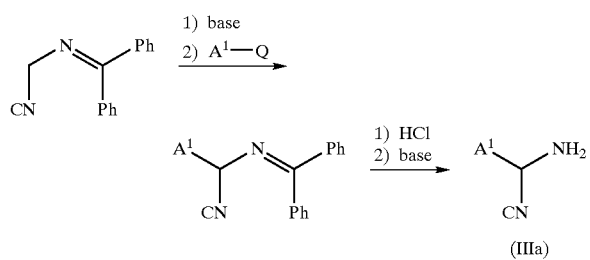

(IIIa)

Compounds of formula III where $R^1$ is alkyl and $R^2$ is cyano or acyl, may be prepared by alkylating analogues where $R^1$ is hydrogen.

Compounds of formula Ic, i.e. compounds of general formula I where L is —C(=N—OR$^b$)— may be prepared from compounds of formula Id where $L^1$ is —C(=NOH)— according to Scheme 4 using methodology known to the skilled chemist. For example compounds of formula Ic where $R^b$ is —C(=O)NHR may be prepared by reaction with R—NCO; compounds where $R^b$ is —C(=O)R may be prepared by reaction with RCOCl and compounds where $R^b$ is —SO$_2$R may be prepared by reaction with RSO$_2$Cl.

Scheme 4

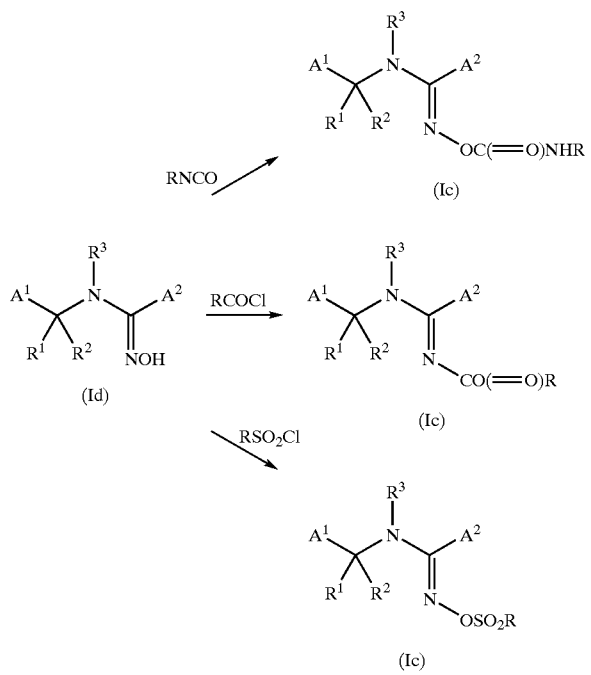

Compounds of formula IIa, i.e. compounds of general formula II where Y is —SR$^b$ may be prepared from compounds of formula Ig, i.e. compounds of formula Ia where $L^1$ is —C(=S)— according to reaction scheme 5. Reaction conditions comprise treating Ig with a base such as sodium hydride followed by reaction with R$^b$Q where Q is a leaving group preferably halogen.

Scheme 5

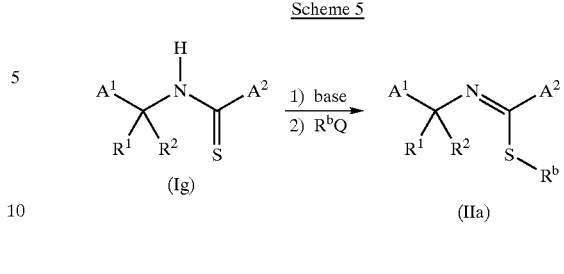

Compounds of formula Ih, i.e. compounds of general formula I where $A^2$ is 2-substituted phenyl which substituent together with $R^3$ and the interconnecting atoms forms a 6-membered ring, may be prepared from compounds of formula Ij by treatment with base, preferably potassium carbonate in acetone, followed by RQ where Q is a leaving group, according to reaction scheme 6.

Scheme 6

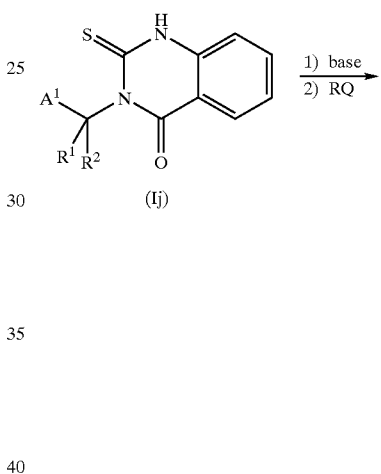

Compounds of general formula Ij, may be prepared by reacting compounds of formula IIIb with compounds of formula VI in the presence of a suitable base, such as triethylamine, according to reaction scheme 7.

Scheme 7

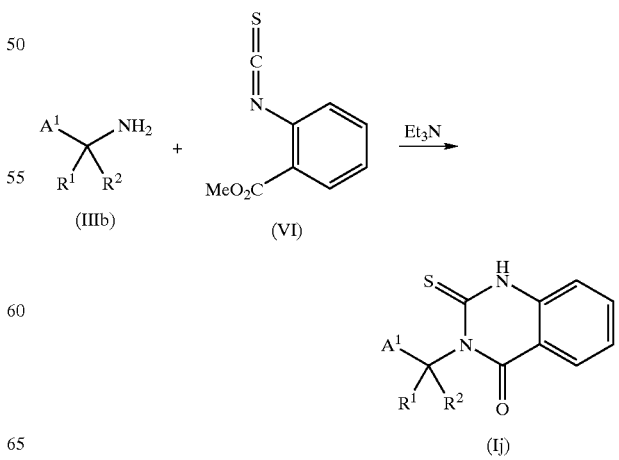

Compounds of formula VI may be prepared by methods known to the skilled chemist from the corresponding amino compound.

Compounds of formula I or II where $A^1$ is pyridyl N-oxide, may be prepared from the corresponding pyridyl derivative by reactions known to the skilled chemist, for example reaction with peracetic acid.

Other methods will be apparent to the chemist skilled in the art, as will be the methods for preparing starting materials and intermediates.

Collections of compounds of formula I and II may also be prepared in a parallel manner, either manually, automatically or semi-automatically. This parallel preparation may be applied to the reaction procedure, work-up or purification of products or intermediates., For a review of such procedures see by S. H. DeWitt in "Annual Reports in Combinatorial Chemistry and Molecular Diversity: Automated synthesis", Volume 1, Verlag Escom 1997, pages 69 to 77.

Furthermore, compounds of the formula I or II may be prepared using solid-supported methods, where the reactants are bound to a synthetic resin. See for example: Barry A. Bunin in "The Combinatorial Index", Academic Press, 1998 and "The tea-bag method" (Houghten, U.S. Pat No. 4,631, 211; Houghten et al., Proc. Natl. Acad. Sci. 1985, 82, 5131–5135).

The invention is illustrated in the following Examples. Structures of isolated, novel compounds were confirmed by NMR and/or other appropriate analyses.

EXAMPLE 1

N-[(3-Chloro-5-trifluoromethyl-2-pyridyl)methyl]-2-furamide (Compound 1)

To a mixture of (3-chloro-5-trifluoromethyl-2-pyridyl) methylamine (1 mmol) in tetrahydrofuran (5 ml) was added triethylamine (1 mmol) at room temperature and the mixture was stirred at room temperature for 1.5 hour. The mixture was added to a solution of 2-furoyl chloride (1 mmol) in tetrahydrofuran (5 ml) at room temperature and left to stir at room temperature overnight. The mixture was evaporated to dryness and the residue washed with water. The solid was filtered, washed with diethyl ether/light petroleum (b.p. 60–80° C.) and dried to give the title product, $_1$H N.M.R. (CDCl$_3$) δ (ppm) 4.9 (2H, d), 6.55 (1H, m), 7.2 (1H, m), 7.5 (1H, s), 7.8 (1H, br.s), 8.0 (1H, s) and 8,8 (1H, s).

EXAMPLE 2

N-[(3-Chloro-5-trifluoromethyl-2-pyridyl)methyl]-5-bromofuramide (Compound 23)

To a mixture of 5-bromofuroic acid (0.19 g) and carbonyl diimidazole (CDI) in dichloromethane was added (3-chloro-5-trifluoromethyl-2-pyridyl)methylamine and the mixture was stirred at room temperature overnight. The mixture was washed with 2M hydrochloric acid, then saturated sodium bicarbonate, dried (MgSO$_4$) and evaporated to give the title product, m.p. 77.8° C.

The following compounds of formula Ik (see Table A), i.e. compounds of general formula I where L is —C(=O)— and $R^1$, $R^2$ and $R^3$ are hydrogen, may be prepared by methods analogous to those of Examples 1 and 2.

TABLE A (Ik)

| Cmp | $A^1$ | $A^2$ | m.p. (° C.) |
|---|---|---|---|
| 1 | 3-Cl-5-CF$_3$-2-pyridyl | 2-furyl | oil |
| 2 | 3-Cl-5-CF$_3$-2-pyridyl | 2-thienyl | oil |
| 3 | 3-Cl-5-CF$_3$-2-pyridyl | 3,5-diMe-isoxazol-4-yl | oil |
| 4 | 3-Cl-5-CF$_3$-2-pyridyl | 5-Me-1,2,3-thiadiazol-4-yl | oil |
| 5 | 3-Cl-5-CF$_3$-2-pyridyl | 6-Cl-3-pyridyl | oil |
| 6 | 3-Cl-5-CF$_3$-2-pyridyl | 5-Cl-6-MeO-3-pyridyl | oil |
| 7 | 3-Cl-5-CF$_3$-2-pyridyl | 2-Cl-4-CF$_3$-pyrimidin-5-yl | oil |
| 8 | 3-Cl-5-CF$_3$-2-pyridyl | 1-Ph-5-CF$_3$-pyrazol-4-yl | oil |
| 9 | 3-Cl-5-CF$_3$-2-pyridyl | 2-Cl-3-pyridyl | oil |
| 10 | 3-Cl-5-CF$_3$-2-pyridyl | 3-pyridyl | oil |
| 11 | 3-Cl-5-CF$_3$-2-pyridyl | 3-Cl-2-thienyl | oil |
| 12 | 3-Cl-5-CF$_3$-2-pyridyl | 2-quinazoline | oil |
| 13 | 3-Cl-5-CF$_3$-2-pyridyl | 3-Cl-2-benzo[b]thienyl | oil |
| 14 | 3-Cl-5-CF$_3$-2-pyridyl | (4-Cl, Me, Me-substituted pyrazolo[3,4-b]pyridinyl) | oil |
| 15 | 3-Cl-5-CF$_3$-2-pyridyl | 2-PhO-3-pyridyl | oil |
| 16 | 3-Cl-5-CF$_3$-2-pyridyl | 2-Me-5-(4-Cl-phenyl)-3-furyl | oil |
| 17 | 3-Cl-5-CF$_3$-2-pyridyl | 5,6-diCl-3-pyridyl | 171–3 |
| 18 | 3-Cl-5-CF$_3$-2-pyridyl | 1-(4-F-2-CF$_3$-benzyl)-imidazol-2-yl | 121 |
| 19 | 3-Cl-5-CF$_3$-2-pyridyl | 2-pyridyl | 112 |

TABLE A-continued (Ik)

$$A^1 \diagdown \underset{\underset{O}{\|}}{\overset{H}{N}} \diagdown A^2$$

| Cmp | A¹ | A² | m.p. (° C.) |
|---|---|---|---|
| 20 | 3-Cl-5-CF₃-2-pyridyl | 5-(3-5-diCl-phenoxy)-2-furyl | 107 |
| 21 | 3-Cl-5-CF₃-2-pyridyl | 4,5-DiBr-2-thienyl | 125 |
| 22 | 3-Cl-5-CF₃-2-pyridyl | isoxazol-5-yl | 110–1 |
| 23 | 3-Cl-5-CF₃-2-pyridyl | 5-Br-2-furyl | 77–8 |
| 24 | 3-Cl-5-CF₃-2-pyridyl | 3-Me-2-thienyl | 134–5 |
| 25 | 3-Cl-5-CF₃-2-pyridyl | 5-MeO-2-benzo[b]thienyl | 122–3 |
| 26 | 3-Cl-5-CF₃-2-pyridyl | 5-NO₂-2-benzo[b]thienyl | 149–51 |
| 27 | 3-Cl-5-CF₃-2-pyridyl | 5-Me-2-thienyl | 129–30 |
| 28 | 3-Cl-5-CF₃-2-pyridyl | 2-4-diMe-5-thiazolyl | 103–4 |
| 29 | 3-Cl-5-CF₃-2-pyridyl | 1-diMe-sulfamoylimidazol-4-yl | 159–60 |
| 30 | 3-Cl-5-CF₃-2-pyridyl | 3,5-diMe-1-Ph-imidazol-4-yl | 158–9 |
| 31 | 3-Cl-5-CF₃-2-pyridyl | 1-Ph-imidazol-4-yl | 126–7 |
| 32 | 3-Cl-5-CF₃-2-pyridyl | 4,6-diMeO-2-(4-Cl-—, —diMe-benzyl)pyrimidin-5-yl | oil |
| 33 | 3-Cl-5-CF₃-2-pyridyl | 5-Br-3-pyridyl | 131–3 |
| 34 | 3-Cl-5-CF₃-2-pyridyl | 2-MeS-3-pyridyl | 131–2 |
| 35 | 3-Cl-5-CF₃-2-pyridyl | 2-MeO-3-pyridyl | 149–50 |
| 36 | 3-Cl-5-CF₃-2-pyridyl | 6-MeO-3-pyridyl | 114–5 |
| 37 | 3-Cl-5-CF₃-2-pyridyl | 2-Cl-6-Me-3-pyridyl | 108–9 |
| 38 | 3-Cl-5-CF₃-2-pyridyl | 2-phenylthiomethylthio-3-pyridyl | 110–1 |
| 39 | 3-Cl-5-CF₃-2-pyridyl | 2-Cl-4-pyridyl | 109–10 |
| 40 | 3-Cl-5-CF₃-2-pyridyl | 2-Ph-quinolin-4-yl | 152–3 |
| 41 | 3-Cl-5-CF₃-2-pyridyl | 2,6-diMeO-3-pyridyl | 181 |
| 42 | 3-Cl-5-CF₃-2-pyridyl | 1-Me-3-indolyl | 171 |
| 43 | 3-Cl-5-CF₃-2-pyridyl | 3-2H-benzopyranyl | 123 |
| 44 | 3-Cl-5-CF₃-2-pyridyl | 4,6-diMeO-pyrimidin-2-yl | 200 |
| 45 | 3-Cl-5-CF₃-2-pyridyl | 4-CF₃-3-pyridyl | oil |
| 46 | 3-Cl-5-CF₃-2-pyridyl | 1-Me-4,5-diBr-2-pyrolyl | oil |
| 47 | 3-Cl-5-CF₃-2-pyridyl | 4,5-diBr-2-pyrolyl | oil |
| 48 | 3-Cl-5-CF₃-2-pyridyl | 4-pyridyl | 124–5 |
| 49 | 3-Cl-5-CF₃-2-pyridyl | 5-Me-pyrazin-2-yl | 118–9 |
| 50 | 3-Cl-5-CF₃-2-pyridyl | 2-Br-4-CF₃-thiazol-5-yl | 72–3 |
| 51 | 3-Cl-5-CF₃-2-pyridyl | 5-Cl-3-benzyloxy-2-benzo[b]furyl | 155–7 |
| 52 | 3-Cl-5-CF₃-2-pyridyl | 3-MeO-2-benzo[b]furyl | oil |
| 53 | 3-Cl-5-CF₃-2-pyridyl | 3-Pr^iO-2-benzo[b]furyl | oil |
| 54 | 3-Cl-5-CF₃-2-pyridyl | 3-BzO-2-benzo[b]furyl | oil |
| 55 | 3-Cl-5-CF₃-2-pyridyl | 3-6-diMeO-2-benzo[b]furyl | oil |
| 56 | 3-Cl-5-CF₃-2-pyridyl | 3-BzO-6-MeO-2-benzo[b]furyl | oil |
| 57 | 3-Cl-5-CF₃-2-pyridyl | 5-Cl-3-MeO-2-benzo[b]furyl | oil |
| 58 | 3-Cl-5-CF₃-2-pyridyl | 4-pyridyl | 154 |
| 59 | 3-Cl-5-CF₃-2-pyridyl | phenylcyclopropyl | oil |
| 60 | 3-Cl-5-CF₃-2-pyridyl | 4-morpholinyl | oil |
| 61 | 3-Cl-5-CF₃-2-pyridyl | 1-(Bu^tOC(=O)-pyrolidin-2-yl | oil |

The ¹H N.M.R. data of those compounds in Table A which were not solid at room temperature are presented below.

Compound 1
¹H N.M.R. (CDCl₃) δ (ppm) 4.9 (2H, d), 6.55 (1H, m), 7.2 (1H, m), 7.5 (1H, s), 7.8 (1H, br.s), 8.0 (1H, s) and 8.8 (1H, s), Compound 2
¹H N.M.R. (CDCl₃) δ (ppm) 4.9 (2H, d), 7.1 (1H, s), 7.5 (1H, m), 7.6 (1H, br.s), 7.65 (1H, m), 8.0 (1H, s) and 8.8 (1H, s).

Compound 3
¹H N.M.R. (CDCl₃) δ (ppm) 2.5 (3H, s), 2.7 (3H, s), 4.9 (2H, d), 7.4 (1H, br.s), 8.0 (1H, s) and 8.8 (1H, s).

Compound 4
¹H N.M.R. (CDCl₃) δ (ppm) 3.05 (3H, s), 4.9 (2H, d), 7.7 (1H, br.s), 8.0 (1H, s) and 8.8 (1H, s).

Compound 5
¹H N.M.R. (CDCl₃) δ (ppm) 4.9 (2H, d), 7.45 (1H, d), 7.8 (1H, br.s), 8.0 (1H, s), 8.2 (1H, m), 8.8 (1H, s) and 8.9 (1H, d).

Compound 6
¹H N.M.R. (CDCl₃) δ (ppm) 4.1 (3H, s), 4.9 (2H, d), 7.7 (1H, br.s), 8.0 (1H, s), 8.2 (1H, s), 8.6 (1H, s) and 8.8 (1H, s).

Compound 7
1H N.M.R. (CDCl₃) δ (ppm) 4.9 (2H, d), 7.7 (1H, br.s), 8.0 (1H, s), 8.7 ( 1H, s) and 9.0 (1H, s).

Compound 8
¹H N.M.R. (CDCl₃) δ (ppm) 4.95 (2H, d), 7.4–7.65 (5H, m), 8.0 (1H, s), 8.1 (1H, s) and 8.8 (1H, s).

Compound 9
¹H N.M.R. (CDCl₃) δ (ppm) 4.6 (2H, s), 4.9 (2H, d), 6.9–7.1 (3H, m), 7.3–7.4 (2H, m), 7.95 (1H, s), 8.1 (1H, br.s) and 8.8 (1H, s).

Compound 10
¹H N.M.R. (CDCl₃) δ (ppm) 4.95 (2H, d), 7.45 (1H, m), 7.85 (1H, s), 8.0 (1H, s), 8.25 (1H, m), 8.8 (2H, m) and 9.2 (1H, s).

Compound 11
¹H N.M.R. (CDCl₃) δ (ppm) 4.9 (2H, d), 7.0 (1H, d), 7.5 (1H, d), 8.0 (1H, s), 8.6 (1H, s) and 8.8 (1H, s).

Compound 12

$^1$H N.M.R. (CDCl$_3$) δ (ppm) 5.05 (2H, d), 7.85–8.0 (3H, m), 8.2–8.3 (2H, m), 8.85 (1H, s), 9.2 (1H, s) and 9.7 (1H, d).

Compound 13

$^1$H N.M.R. (CDCl$_3$) δ (ppm) 5.0 (2H, d), 7.55 (2H, m), 7.85 (1H, m), 7.95 (1H, m), 8.0 (1H, s) and 8.85 (1H, s).

Compound 14

$^1$H N.M.R. (CDCl$_3$) δ (ppm) 2.75 (3H, s), 4.1 (3H, s), 5.0 (2H, d), 8.0 (1H, s), 8.75 (1H, s) and 8.9 (1H, s).

Compound 15

$^1$H N.M.R. (CDCl$_3$) δ (ppm) 4.50 (2H, d), 7.3 (4H, m), 7.5 (2H, t), 7.95 (1H, s), 8.25 (1H, m), 8.55 (1H, br.s), 8.6 (1H, s) and 8.7 (1H, s).

Compound 16

$^1$H N.M.R. (CDCl$_3$) δ (ppm) 2.75 (3H, s), 4.9 (2H, d), 6.8 (1H, s), 7.35 (2H, d), 7.65 (2H, d), 8.0(1H, s) and 8,8 (1H, s).

Compound 32

$^1$H N.M.R. (CDCl$_3$) δ (ppm) 1.75 (6H, d, 2×Me), 3.92 (6H, d, 2×Me), 4.89 (2H, d, 2×Me), 7.20–30 (4H, m, Ar), 7.85 (1H, s, NH), 7.95 (1H, s, py—H) and 8.70 (1H, s, py—H).

Compound 45

$^1$H N.M.R. (CDCl$_3$) δ (ppm) 4.92 (2H, d, —CH$_2$—), 7.51 (1H, br.s, NH), 7.61 (1H, d, pyH), 8.00 (1H, s, py—H), 8.90 (1H, d, py—H) and 8.96 (1H, s, pyH).

Compound 46

$^1$H N.M.R. (CDCl$_3$) δ (ppm) 3.98 (3H, s), 4.82 (2H, d), 6.80 (s, Ar—H), 7.36 (1H, br.s), 7.97 (s. Ar—H) and 8.77 (s. ArH).

Compound 47

$^1$H N.M.R. (DMSO) δ (ppm) 4.73 (2H, d), 7.00 (s. Ar—H), 8.46 (ArH, s), 8.76 (NH, t), 8.91 (1H, s, Ar) and 12.75 (br.s, NH).

Compound 52

$^1$H N.M.R. (CDCl$_3$) δ (ppm) 4.45 (3H, s), 5.00 (2H, d), 7.35 (1H, t), 7.45 (1H, t) 7.60 (1H, d), 7.80 (1H, d), 8.00 (1H, s), 8.40 (1H, t) and 8.80 (1H, s)

Compound 53

$^1$H N.M.R. (CDCl$_3$) δ (ppm) 1.57 (6H, d), 5.00 (2H, d) 5.15 (1H, m), 7.35 (1H, t), 7.45 (1H, t), 7.60 (1H, d), 7.75 (1H, d), 8.00 (1H, s), 8.70 (1H, t) and 8.80 (1H, s).

Compound 54

$^1$H N.M.R. (CDCl$_3$) δ (ppm) 4.95 (2H, d), 5,60 (2H, s), 7.35 (1H, t), 7.40–7.60 (7H, m), 7.80 (1H, d), 7.95 (1H, s), 8.30 (1H, s) and 8.55 (1H, t).

Compound 55

$^1$H N.M.R. (CDCl$_3$) δ (ppm) 3.90 (3H, s), 4.35 (3H, s), 5.00 (2H, d), 6.95 (1H, dd), 7.05 (1H, d), 7.65 (1H, d), 8.00 (1H, s), 8.55 (1H, t) and 8.80 (1H, s).

Compound 56

$^1$H N.M.R. (CDCl$_3$) δ (ppm) 3.90 (3H, s), 4.95 (2H, d), 5.60 (2H, s), 6.95 (1H, dd), 7.05 (1H, d), 7.40 (3H, m), 7.55 (2H, m), 7.65 (1H, d), 7.95 (1H, s), 8.3 (1H, s) and 8.40 (1H, t).

Compound 57

$^1$H N.M.R. (CDCl$_3$) δ (ppm) 4.40 (3H, s), 5.00 (2H, d), 7.40 (1H, d), 7.50 (1H, d), 7.80 (1H, s), 8.00 (1H, s), 8.40 (1H, t) and 8.80 (1H, s).

Compound 59

$^1$H N.M.R. (CDCl$_3$) δ (ppm) 1.3 (1H, m), 1.65 (1H, m), 1.85 (1H, m), 2.55 (1H, m), 4.75 (2H, d), 7.1–7.3 (5H, m), 7.95 (1H, s) and 8.7 (1H, s).

Compound 60

$^1$H N.M.R. (CDCl$_3$) δ (ppm) 3.4 (4H, dd), 3.8 (4H, dd), 4.75 (2H, d), 6.1 (1H, br.s), 7.95 (1H, s) and 8.95 (1H, s).

Compound 61

$^1$H N.M.R. (CDCl$_3$) δ (ppm) 5.05 (2H, d), 7.4–7.6 (4H, m), 7.8 (1H, d), 7.9–8.05 (3H, m) 8.4 (1H, d) and 8.75 (1H, s).

EXAMPLE 3

N-[1-(3-Chloro-5-trifluoromethyl-2-pyridyl)-1-cyanoethyl]-2,6-dichlorobenzamide

Compound 110

To a suspension of 1-(3-chloro-5-trifluorormethyl)-2-pyridyl)- 1 -cyanoethylammonium chloride (0.51 g) in drv dichloromethane (10 ml) was added dry triethylamine (0.3 ml) followed by dropwise addition of 2,6-dichlorobenzoyl chloride (0.42 g) and the mixture was stirred for 4 hours. The reaction mixture was washed with aqueous potassium carbonate solution (2×10 ml) and the organic phase was dried (MgSO$_4$). The filtrate was evaporated onto silica and purified by silica gel chromatography gradient eluting with diethyl ether/dichloromethane (0–20%) to give the title compound, m.p. 166–7° C.

Preparation of Starting Materials a) (3-Chloro-5-trifluoromethyl-2-pyridyl)[(diphenylmethylene)amino]acetonitrile To a suspension of 60% sodium hydride (4.0 g) in dry dimethylformamide at 0–2° C. under nitrogen was dropwise added a solution of N-(diphenylmethylene)aminoacetonitrile (11.1 g) in dry dimethylformamide (60 ml) and the mixture was stirred for 1 hour at 0° C., 2,3-Dichloro-5-trifluoromethyl pyridine (7 ml) in dry dimethylformamide (20 ml) was added dropwise over 10 minutes. The mixture was stirred at 0° C. for 30 minutes and then warmed to 22° C. over 3 hours. The mixture was re-cooled to less than 10° C., and ethanol (3 ml) was added dropwise and stirring continued for 15 minutes. The mixture was poured as a thin stream into a stirred mixture of diethyl ether (500 ml) and 20% saturated aqueous ammonium chloride solution. The phases were separated and the organic phase was washed with 20% saturated aqueous ammonium chloride solution (2×150 ml). The organic phase was dried over anhydrous magnesium sulphate, filtered and evaporated onto flash silica (50 g). Chromatography over silica eluting with 5–20% diethyl ether in 40/60° Bp petrol gave the title compound, m.p. 108–110° C.

b) 2-(3-Chloro-5-trifluoromethyl-2-pyridyl)-2-[(diphenylmethylene)amino]propionitrile To a stirred solution of potassium tert-butoxide (1.91 g) in dry tetrahydrofuran (50 ml) at −60° C. under nitrogen was dropwise added a solution of the product from stage a) above (5 g) in dry tetrahydrofuran (20 ml). The mixture was stirred at 60° C. for 15 minutes then methyl iodide (1.5 ml) was added dropwise and the mixture warmed to 22° C. over 18 hours. The solvent was evaporated in vacuo and the residue was partitioned between diethyl ether and 50% saturated aqueous ammonium chloride. The aqueous phase was ether extracted (2×50 ml) and the pooled organic extracts were dried over anhydrous magnesium sulphate. The filtered organic phase was evaporated onto flash silica (20 g). Chromatography over silica eluting with 10–30% diethyl ether in light petroleum (b.p. 40–60° C.) gave the title compound, $^1$H N.M.R. CDCl$_3$ δ (ppm) 2.24 (3H, s, CH$_3$), 7.10–7.62 (1H, m, Ar—H), 7.90 (1H, s, py—H) and 8.54 (1H, s, py—H).

c) 2-Amino-2-(3-chloro-5-trifluoromethyl-2-pyridyl) propionitrile Hydrochloride

To a vigorously stirred solution of the product from stage b) (5.5 g) in diethyl ether (100 ml) under nitrogen was added 2M aqueous hydrogen chloride (100 ml) and stirring continued for 36 hours. The phases were separated and the organic phase was extracted with 2M aqueous hydrogen chloride (2×20 ml). The combined aqueous phases were extracted with diethyl ether (2×20 ml) and the organic extracts discarded. The aqueous phase was evaporated in vacuo then azeotroped with toluene (3×50 ml). Trituration with diethyl ether followed by filtration and vacuum drying gave the title compound, m.p. 165–70° C.

The following compounds of formula Im (see Table B), i.e. compounds of general formula I where $A^1$ is 3-Cl-5-$CF_3$-2-pyridyl, L is —C(=O)— and $R^3$ is hydrogen, may be prepared by methods analogous to those of Examples 1, 2 and/or 3.

TABLE B (Im)

| Cmp | $R^1$ | $R^2$ | $A^2$ | m.p. (° C.) |
|---|---|---|---|---|
| 101 | ethoxycarbonyl | H | 5-Cl-6-MeO-3-pyridyl | 148–50 |
| 102 | ethoxycarbonyl | H | 2-thienyl | oil |
| 103 | Me | H | 2-furyl | 134 |
| 104 | Me | H | 2-thienyl | 121 |
| 105 | piperidinyl | H | 4-$CF_3$-3-pyridyl | |
| 106 | Me | H | 4-morpholinyl | 139 |
| 107 | allyl | H | 2,6-diCl-phenyl | 122 |
| 108 | cyano | H | 2-Cl-6-F-phenyl | 114 |
| 109 | cyano | H | 2-Br-6-Cl-phenyl | 179 |
| 110 | cyano | Me | 2,6-diCl-phenyl | 166 |
| 111 | cyano | Me | 2-Cl-6-F-phenyl | 174 |
| 112 | cyano | Me | 2-Br-6-Cl-phenyl | oil |
| 113 | cyano | H | 2,4-diCl-phenyl | 110 |
| 114 | cyano | Me | 2,4-diCl-phenyl | 160 |
| 115 | cyano | H | 4-Cl-phenyl | oil |
| 116 | cyano | H | 3,5-diCl-phenyl | 135 |
| 117 | cyano | Me | 3,4-diCl-phenyl | 207 |
| 118 | cyano | Me | 3,4-diCl-phenyl | 207 |
| 119 | cyano | Me | 4-F-phenyl | 201 |
| 120 | hydroxy | H | 4,5-diCl-phenyl | oil |

The $^1$H N.M.R. data of those compounds in Table B which were not solid at room temperature presented below.

Compound 102
$^1$H N.M.R. ($CDCl_3$) δ (ppm) 1.23 (1H, t), 4.25 (1H, m), 6,46 (1H, d), 7.12 (1H, m), 7.44 (1H, d), 7.63 (1H, d) and 8.78 (1H, s).

Compound 112
$^1$H N.M.R. ($CDCl_3$) δ (ppm) 2.32 (3H, s, Me), 7.22 (1H, m, Ar—H), 7.40 (1H, d, Ar—H), 7.54 (1H, d, Ar—H), 8.14 (1H, d, py—H), 8.36 (1H, s, NHCO) and 8.76 (1H, d, py—H).

Compound 115
$^1$H N.M.R. ($CDCl_3$) δ (ppm) 6.54 (1H, d, CHCN), 7.46 (2H, 2×Ar—H), 7.80 (2H, m, 2×Ar—H), 7.9 (1H, d, NHCO), 8.12 (1H, d, py—H and 8.80 (1H, d, py—H).

Compound 120
$^1$H N.M.R. ($CDCl_3$) δ (ppm) inter alia 7.6 (1H, d, Ar—H), 7.75 (2H, d, 2×Ar—H), 8.18 (1H, d, py—H), 8.84 (1H, d, pyH).

EXAMPLE 4

N-[(3-Chloro-5-trifluoromethyl-2-pyridyl)methyl]-N-[(cyanoimino)methyl]-4-chlorobenzamide
(Compound 205)

This compound was prepared in analogous fashion to Example 1 using 2-chlorobenzoyl chloride and the starting material described below.

Preparation of Starting Materials

N-Cyano-N'-(3-chloro-5-trifluoromethyl-2-pyridylmethyl)formamidine

To a stirred suspension of (3-chloro-5-trifluoromethyl-2-pyridyl)methylammonium hydrochloride (19 g) in ethanol (180 ml) was added triethylamine (10.7 ml) and stirring was continued for 15 minutes. Ethoxycyanoimidate (8.29 g) in ethanol (20 ml) was then added dropwise and stirred at room temperature for 20 minutes. The solvent was removed in vacuo and the residue partitioned between diethyl ether and water. The organic layer was separated and filtered. The filtrate was dried ($MgSO_4$) and evaporated to give the title product, m.p. 106–8° C.

The following compounds of formula In (see Table C), i.e. compounds of general formula I where $A^1$ is 3-Cl-5-$CF_3$2-pyridyl, L is —C(=O)— and $R^2$ is hydrogen, may be prepared by methods analogous to those of Examples 1, 2, 3 and/or 4.

TABLE C (In)

| Cmp | $R^1$ | $R^3$ | $A^2$ | m.p. (° C.) |
|---|---|---|---|---|
| 201 | ethoxycarbonyl | Et | 2-thienyl | oil |
| 202 | methoxycarbonyl | Pr | 2-furyl | |
| 203 | ethoxycarbonyl | Me | 2-thienyl | |
| 204 | H | N-cyano-iminomethyl | 4-$Bu^t$-phenyl | |
| 205 | H | N-cyano-iminomethyl | 4-Cl-phenyl | oil |
| 206 | H | N-cyano-iminomethyl | 2-$CF_3$-phenyl | oil |
| 207 | H | N-cyano-iminomethyl | 4-$CF_3$O-phenyl | |
| 208 | H | N-cyano-iminomethyl | 4-$CF_3$O-phenyl | |
| 209 | H | N-cyano-iminomethyl | 4-$CF_3$O-phenyl | isomer of 208 |

TABLE C-continued (In)

| Cmp | R$^1$ | R$^3$ | A$^2$ | m.p. (° C.) |
|---|---|---|---|---|
| 210 | H | N-cyano-iminomethyl | 3,5-diCl-phenyl | |
| 211 | H | N-cyano-iminomethyl | 3-Pr$^i$O-phenyl | |
| 212 | H | N-cyano-iminomethyl | 3-PhO-phenyl | |
| 213 | H | N-cyano-iminomethyl | 4-biphenylyl | |
| 214 | H | N-cyano-iminomethyl | 2-tolyl | |
| 215 | H | N-cyano-iminomethyl | 3-CN-phenyl | |

The $^1$H N.M.R. data of those compounds in Table B which were not solid at room temperature are presented below.

Compound 205
$^1$H N.M.R. (CDCl$_3$) δ (ppm) 5.24–5.36 (2H, s, CH$_2$), 7.45–7.56 (4H, m, Ar—H), 7.82–7.88 (1H, s, Ar—H), 8.50–8.56 (1H, s, N=CH) and 8.84–8.96 (1H, m, ArH).

Compound 206
$^1$H N.M.R. (CDCl$_3$) δ (ppm) 5.3–5.5 (2H, m, CH$_2$), 7.6–7.8 (4H, m, Ar—H), 7.9 (1H, s), 8.5 (1H, m, N=CH) and 8.65 (1H, s, ArH).

EXAMPLE 5

N-[(3-Chloro-5-trifluoromethyl-2-pyridyl)methyl]-2-nitrophenylacetamide Oxime
(Compound 304)

This compound was prepared in analogous fashion to Example 1 replacing furoyl chloride with 2-nitro-α-chlorobenzaldoxime (see stage b below).

Preparation of Starting Materials
a) 2-Nitrobenzaldoxime

To a solution of 2-nitrobenzaldehyde (115 g) and hydroxylamine hydrochloride (6.6 g) in ethanol (110 ml) and water (4 ml) was added sodium acetate (13.6 g) and the mixture was stirred at room temperature for 4 hours. The mixture was poured into water (500 ml) and the mixture filtered to give the title product.

b) 2-Nitro-α-chlorobenzaldoxime

Through an ice-cold solution of the product from stage a) (10.7 g) in concentrated hydrochloric acid (60 ml) and water (12.3 ml) was bubbled chlorine gas for one hour. The mixture was then stirred at room temperature overnight. The mixture was filtered to give the title product.

EXAMPLE 6

N-[(3-Chloro-5-trifluoromethyl-2-pyridyl)methyl]-2-nitrophenylacetamide-O-(phenylcarbamoyl)oxime
(Compound 305)

To a stirred mixture of the product from Example 5 (0.9 g) and 2,6-dichlorophenyl isocyanate (0.33 g) in acetonitrile (50 ml) was added three drops of triethylamine. The mixture was heated to reflux for 2 hours. On cooling the solvent was removed, and the residue purified by silica gel chromatography to give the title product, m.p. 138–40° C.

The following compounds of formula Ip (see Table D), i.e. compounds of general formula I where A$^1$ is 3-Cl-5-CF$_3$-2-pyridyl, R$^1$, R$^2$ and R$^3$ are hydrogen and L is —(C=X)—, may be prepared by methods analogous to those of Examples 5 and 6.

TABLE D (Ip)

| Cmp | X | A$^2$ | m.p./° C. |
|---|---|---|---|
| 301 | =NOH | 2,6-diCl-phenyl | 189–91 |
| 302 | =NOC(=O)N—Ph | 2,6-diCl-phenyl | 168–70 |
| 303 | =NOC(=O)Et | 2,6-diCl-phenyl | 89–92 |
| 304 | =NOH | 2-NO$_2$-phenyl | 122–6 |
| 305 | =NOC(=O)-2,6-diClPh | 2-NO$_2$-phenyl | 138–40 |
| 306 | =NOS(=O)$_2$Me | 2-NO$_2$-phenyl | oil |

The $^1$H N.M.R. data of the compound in Table D which was not solid at room temperature presented below.

Compound 306

3.1 (3H, s), 4.4 (2H, d) 7.15 (1H, br.t), 7.65 (1H, m), 7.8 (2H, m), 7.8 (2H, m), 7.9 (1H, s), 8.25 (1H, d) and 8.8 ($^1$H, s).

EXAMPLE 7

N$^1$-[(3-Chloro-5-trifluoromethyl]-2-pyridyl)methyl-2-chlorobenzamidine Hydrochloride Compound 307

This compound was prepared from (3-chloro-5-trifluoromethyl-2-pyridl)methylammonium hydrochloride and methyl 2-chlorothiobenzimidate Hydrogen iodide salt, using methods described in the R C Schnur, *J. Org. Chem.* 1979, Vol,44, No.21, 3726. Methyl 2-chlorothiobenzimidate hydrogen iodide salt was prepared using methods described in Matsuda et al, *Synthetic Communications*, 1997, 2393. $^1$H N.M.R. (CDCl$_3$) δ (ppm) (5.10 (2H, d, CH$_2$), 7.60 (1H, m. ArH), 7.65–7.80 (3H, m. ArH), 8.60 (3H, mm ArH) 8.60 (1H, m, py—H), 9.04 (1H, m, py—H), 9,80–10.00 (1H, br.m, =NH.HCl) and 10.55 (1H, br.m, NH).

EXAMPLE 8

N-(α-Allylthio-2-chlorobenzylidene)-(3-chloro-5-trifluoromethyl-2-pyridyl)methylamine (Compound 403)

To a mixture of sodium hydride (0.33 g) in tetrahydrofuran (10 ml) was added N-[(3-chloro-5-trifluoromethyl-2-pyridyl)methyl]-2-chlorobenzenethioamide (for preparation see PCT/GB/99/00304) (3.07 g) in tetrahydrofuran (50 ml) dropwise with stirring for 20 minutes until effervescence had ceased. Allyl bromide (0.09 g) in tetrahydrofuran (5 ml) was added to the reaction mixture, and the solution was stirred overnight at room temperature. The mixture was evaporated to dryness and the residue partitioned between dichloromethane (10 ml), water (5 ml) and brine (5 ml). The organic phase was separated and the solvent and any residual water evaporated in vacuo. The residue was purified by silica gel chromatography, gradient eluting with light petroleum (b.p. 60–80° C.)/diethyl ether to give the title product.

The following compounds of formula IIb (see Table E), i.e. compounds of general formula II where $A^1$ is 3-Cl-5-CF$_3$-2-pyridyl, $A^2$ is 2-Cl-phenyl and $R^1$ and $R^2$ are hydrogen, may be prepared by methods analogous to those of Example 8.

TABLE E (IIb)

| Cmp | Y | mass spectral data [m/z (API)] |
|---|---|---|
| 401 | SMe | 379 (M+H)$^+$ |
| 402 | SEt | 393 (M+H)$^+$ |
| 403 | allylthio | 405 (M+H)$^+$ |
| 404 | benzylthio | 455 (M+H)$^+$ |
| 405 | 2-Me-benzylthio | 469 (M+H)$^+$ |
| 406 | 4-Cl-benzylthio | 489 (M+H)$^+$ |

EXAMPLE 9

N-{[3-Chloro-5-(trifluoromethyl)-2-pyridyl]methyl}-4,5-dichloror-3,6-epoxy-1,2-dicarboximide (Compound 503)

To a mixture of (3-chloro-5-trifluoromethyl-2-pyridyl)methylamine (1 mmol) in xylene (5 ml) was added triethylamine (1 mmol) at room temperature and the mixture was stirred at room temperature for 1.5 hour. The mixture was filtered and the filtrate was added to 4,5-dichloro-3,6-epoxy-1,2-dicarboxylic anhydride (1 mmol) in xylene (5 ml) at room temperature. The reaction mixture was heated at 130° C. for 48 hours. On cooling, the solvent was removed, the residue was washed with diethyl ether/light petroleum (b.p. 60–80° C.) and dried to give the title product.

EXAMPLE 10

3-(3-Chloro-5-trifluoromethyl-2-pyridyl)methyl-1,2,3,4-tetrahydro-4-oxo-2-thioxoquinazoline (Compound 504)

To a suspension of [3-chloro-5-(trifluoromethyl)-2-pyridyl]methylammonium chloride (0.12 g) and 2-(methoxycarbonyl)phenylthioisocyanate (0.10 g) in dry tetrahydrofuran (10 ml) was added 10 drops of triethylamine. The mixture was stirred at room temperature overnight. The solvent was removed by evaporation in vacuo and the product was extracted with ethyl acetate and washed with 2M hydrochloric acid. The organic layer was collected and evaporated in vacuo to give the title product. $^1$H N.M.R. (CDCl$_3$) δ (ppm) 6.15 (2H, s), 7.15 (1H, d), 7.35 (1H, t), 7.7 (1H, t), 7.9 (1H, s), 8.18 (1H, d), 8.75 (1H, s) and 10.2 (1H, s, NH).

EXAMPLE 11

(3-(3-Chloro-5-trifluoromethyl-2-pyridyl)methyl-3,4-dihydro-4-oxo-2-[(4-chlorobenzyl)thio]quinazoline (Compound 507)

This compound was prepared from the product of Example 10 and 4-chlorobenzylbromide in analogous fashion to Example 8, m.p. 137° C.

EXAMPLE 12

N-[(3-Chloro-5-trifluoromethyl-2-pyridyl)methyl]phthalimide (Compound 518)

A mixture of phthalic anhydride (0.601 g), 3-chloro-5-trifluoromethyl-2-pyridyl)methylammonium hydrochloride (1.0 g) and powdered potassium carbonate (0.28 g) in dimethylformamide was stirred at 148° C. for 7 hours. On cooling, water (10 ml) was added and the mixture filtered to give a solid. The solid was dissolved in ethyl acetate, dried (MgSO4) and the solvent removed. The residue was triturated from diethyl ether to give the title product, m.p. 145–6° C.

EXAMPLE 13

2-{[3-Chloro-5-(trifluoromethyl)-2-pyridyl]methyl}-3-hydroxy-1-indanone

Compound 516

To an ice-cooled solution of the product from Example 12 (1.23 g) in methanol (12.3 ml) was added sodium borohydride portionwise over 5 minutes and stirring was continued overnight. The mixture was partitioned between saturated ammonium chloride (50 ml) and ethyl acetate (50 ml). The layers were separated and the organic layer was dried (MgSO$_4$), Evaporation gave the title compound, m.p. 174–8° C.

The following compounds of formula Iq (see Table F), i.e. compounds of general formula I where $A^1$ is 3-Cl-5-CF$_3$-2-pyridyl, $R^1$ and $R^2$ are hydrogen, and $R^3$ and $A^2$ together with the interconnecting atoms form a ring, may be prepared by methods analogous to those of Examples 9, 10, 11, 12 and/or 13. Compounds 514, 515 and 517 were prepared be simple alkylation of compound 516; such methods are familiar to skilled chemists.

TABLE F
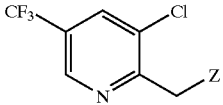
| Cmp | Z | m.p. (° C.) |
|---|---|---|
| 501 | 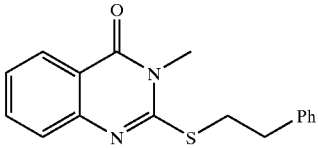 | 126 |
| 502 | 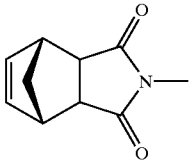 | oil |
| 503 | 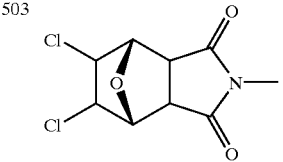 | oil |
| 504 | 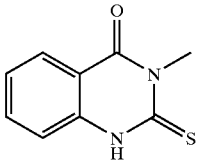 | oil |
| 505 | 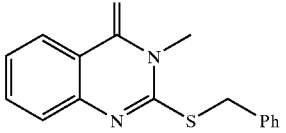 | 148–50 |
| 506 | 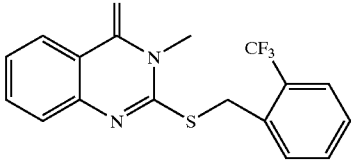 | 134–6 |
| 507 | 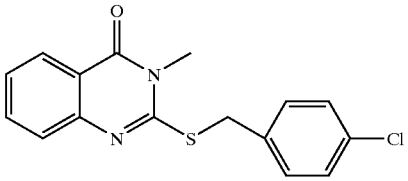 | 137 |
TABLE F-continued
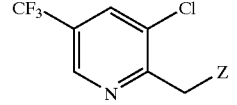
| Cmp | Z | m.p. (° C.) |
|---|---|---|
| 508 | 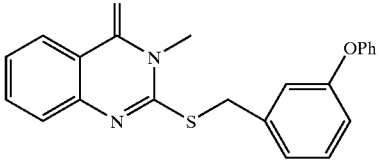 | 105 |
| 509 | 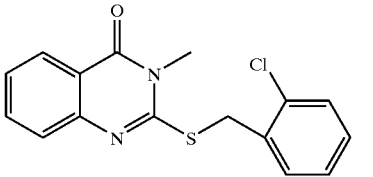 | 149 |
| 510 | 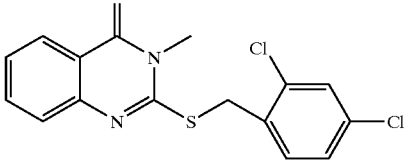 | 85–8 |
| 511 | 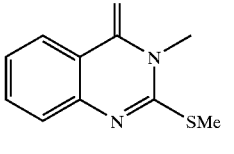 | oil |
| 512 | 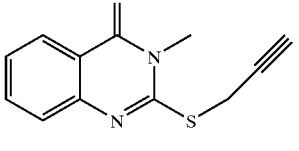 | oil |
| 513 | 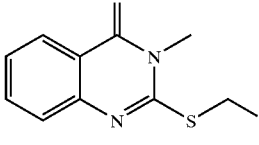 | oil |
| 514 | 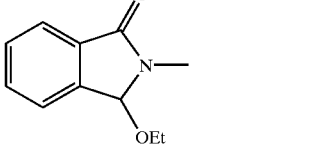 | oil |
| 515 | 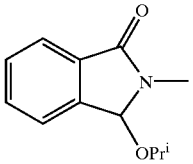 | oil |

TABLE F-continued

CF₃ on pyridine with Cl, CH₂Z

| Cmp | Z | m.p. (° C.) |
|---|---|---|
| 516 | isoindolin-1-one with OH at 3-position | 174–8 |
| 517 | isoindolin-1-one with OMe at 3-position | oil |
| 518 | phthalimide (isoindoline-1,3-dione) | 145–6 |

The ¹H N.M.R. data of those compounds in Table D that were not solid at room temperature are presented below.

Compound 502
¹H N.M.R. (CDCl₃) δ (ppm) 1.6 (1H, d), 1.8 (1H, d), 2.4 (4H, s), 4.9 (2H, s), 6.15 (2H, s), 7.9(1H, s) and 8.6 (1H, s).

Compound 503
¹H N.M.R. (CDCl₃) δ (ppm) 3.25 (1H, d), 3.85 (1H, d), 3.95 (1H, d), 4.35 (1H, m), 4.9 (1H, s), 4.95 (2H, s), 5.1 (1H, m), 7.9 (1H, s) and 8.65 (1H, s).

Compound 504
¹H N.M.R. (CDCl₃) δ (ppm) 6.15 (2H, s), 7.15 (1H, d), 7.35 (1H, t), 7.7 (1H, t), 7.9 (1H, s), 8.18 (1H, d), 8.75 (1H, s) and 10.2(1H, s, NH).

Compound 511
¹H N.M.R. (CDCl₃) δ (ppm) 2.7 (3H, s), 5.7 (2H, s), 7.25 (12H, t), 7.65 (1H, d), 7.75 (1H, t), 7.95 (1H, s), 8.25 (1H, d) and 8.6 (1H, s).

Compound 512
¹H N.M.R. (CDCl₃) δ (ppm) 2.25 (1H, t), 4.1 (2H, d), 5.65 (2H, s), 7.45 (1H, t), 7.65 (1H, d), 7.75 (1H, t), 7.95 (1H, s), 8.25 (1H, d) and 8.6 (1H, s).

Compound 513
¹H N.M.R. (CDCl₃) δ (ppm) 3.8 (3H, s), 4.05 (2H, s), 5.65 (2H, s), 7.45 (1H, t), 7.55 (1H, d), 7.75 (1H, t), 7.95 (1H, s), 8.25 (1H, d) and 8.6 (1H, s).

Compound 514
¹H N.M.R. (CDCl₃) δ (ppm) 1.1 (3H, t), 3.1 (1H, m), 3.3 (2H, s), 4.6 (1H, d), 5.4 (1H, d), 6.1 (1H, s), 7.4–7.6 (3H, m), 7.9(2H, m) and 8,6(1H, s).

Compound 515
¹H N.M.R. (CDCl₃) δ (ppm) 1.1 (3H, d), 1.2 (3H, d), 3.7 (1H, m), 4.7 (1H, d), 5.4 (1H, d), 6.1 (1H, s), 7.4–7.6 (3H, m), 8.8–8.9 (2H, m) and 8.6 (1H, s).

Compound 517
¹H N.M.R. (CDCl₃) δ (ppm) 3.0 (3H, m), 4.6 (1H, d), 5.4 (1H, d), 6.1 (1H, s), 7.5–7.7 (3H, m), 7.9 (2H, m) and 8.6 (1H, s).

TEST EXAMPLE

Compounds were assessed for activity against one or more of the following:

*Phytophihora infestans*: late tomato blight
*Plasmopara viticola*: vine downy mildew
*Erysiphe gramrinis* f. sp. tritici: wheat powdery mildew
*Pyricularia oryzae*: rice blast
*Leptosphaeria nodorum*: glume blotch Aqueous solutions or dispersions of the compounds at the desired concentration, including a wetting agent, were applied by spray or by drenching the stem base of the test plants, as appropriate. After a given time, plants or plant parts were inoculated with appropriate test pathogens before or after application of the compounds as appropriate, and kept under controlled environmental conditions suitable for maintaining plant growth and development of the disease. After an appropriate time, the degree of infection of the affected part of the plant was visually estimated. Compounds are assessed on a score of 1 to 3 where 1 is little or no control, 2 is moderate control and 3 is good to total control. At a concentration of 500 ppm (w/v) or less, the following compounds scored 2 or more against the fungi specified.

*Phyiophihora infestans*
7, 14, 34, 37, 45, 104, 108, 110, 111, 112, 206, 210 and 214.

*Plasmopara viticola:*
7, 14, 34, 37, 41, 42, 43, 44, 45, 109, 110, 111, 112, 206, 214 and 301.

*Erysiphe graminis* f. sp. tritici:
2, 4, 15, 31, 108 and 516.

*Pyricularia oryzae*
4, 39, 41, 108, 109, 113, 116, 201, 215, 512 and 516.

*Leptosphaeria nodorum*
11, 15, 46, 48, 49 and 50.

What is claimed is:
1. A method of preventing or reducing phytopathogen infestation at a locus in need of such prevention or reduction comprising the step of contacting said locus with at least one compound of formula (I) or (II) or a salt thereof:

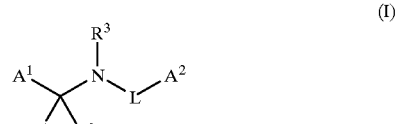

(I)

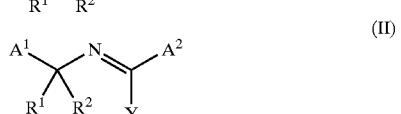

(II)

wherein
$A^1$ is a 2-pyridyl or its N-oxide, each of which may be substituted by up to four groups at least one of which is haloalkyl;

$A^2$ is heterocyclyl or carbocyclyl, each of which may be substituted;

$R^1$ and $R^2$, which may be the same or different, are $R^b$, cyano, nitro, halogen, —$OR^b$, —$SR^b$ or optionally substituted amino, or $R^1$ or $R^2$ together with the carbon to which they are attached may form a 3-, 4-, 5- or 6-, carbo- or heterocyclic ring, which may be substituted;

$R^3$ is $R^b$, —$OR^b$, or —$N(R^b)_2$, cyano, N-substituted iminomethyl or nitro; or $R^3$ and $A^2$, together with the interconnecting atoms, may for a 5- or 6-membered ring;

L is —C(=X)— or —SO$_2$—, where X is oxygen, sulfur, N—OR$^b$, N—R$^b$ or N—N(R$^b$)$_2$; and Y is halogen, —OR$^b$, —SR$^b$, —N(R$^b$)$_2$, —NR$^b$(OR$^b$) or —NR$^b$N(R$^b$)$_2$; and R$^b$, which may be the same or different is alkyl, alkenyl, alkynyl, carbocyclyl or heterocyclyl, each of which may be substituted; or hydrogen or acyl, or two adjacent R$^b$ groups together with the interconnecting atoms, may form a 5- or 6-membered ring;

with the proviso that when A$^1$ is 2-pyridyl, R$^1$ is hydrogen, R$^2$ is hydrogen, optionally substituted alkyl or acyl, L is —C(=X)— or —SO2—, X is oxygen or sulfur and R$^3$ is hydrogen or optionally substituted alkyl, A$^2$ is not optionally substituted phenyl.

2. A pesticidal composition comprising agriculturally acceptable diluent or carrier and a compound of formula (I) or (II), or a salt thereof:

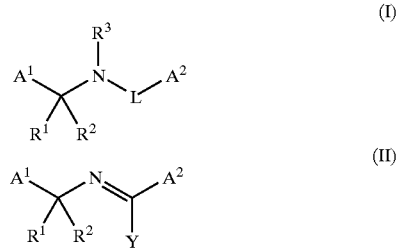

wherein

A$^1$ is a 2-pyridyl or its N-oxide, each of which may be substituted by up to four groups at least one of which is haloalkyl;

A$^2$ is heterocyclyl or carbocyclyl, each of which may be substituted;

R$^1$ and R$^2$, which may be the same or different, are R$^b$, cyano, nitro, halogen, —OR$^b$, —SR$^b$ or optionally substituted amino, or R$^1$ or R$^2$ together with the carbon to which they are attached may form a 3-, 4-, 5- or 6-, carbo- or heterocyclic ring, which may be substituted;

R$^3$ is R$^b$, —OR$^b$, or —N(R$^b$)$_2$, cyano, N-substituted iminomethyl or nitro; or R$^3$ and A$^2$, together with the interconnecting atoms, may for a 5- or 6-membered ring;

L is —C(=X)— or —SO$_2$—, where X is oxygen, sulfur, N—OR$^b$, N—R$^b$ or N—N(R$^b$)$_2$; and Y is halogen, —OR$^b$, —SR$^b$, —N(R$^b$)$_2$, —NR$^b$(OR$^b$) or —NR$^b$N(R$^b$)$_2$; and R$^b$, which may be the same or different is alkyl, alkenyl, alkynyl, carbocyclyl or heterocyclyl, each of which may be substituted; or hydrogen or acyl, or two adjacent R$^b$ groups together with the interconnecting atoms, may form a 5- or 6-membered ring;

with the proviso that when A$^1$ is 2-pyridyl, R$^1$ is hydrogen, R$^2$ is hydrogen, optionally substituted alkyl or acyl, L is —C(=X)— or —SO$_2$—, X is oxygen or sulfur and R$^3$ is hydrogen or optionally substituted alkyl, A$^2$ is not optionally substituted phenyl.

3. A method of combating pests at a locus infested or liable to be infested therewith, which comprises applying to the locus a compound of formula (I) or (II), or a salt thereof:

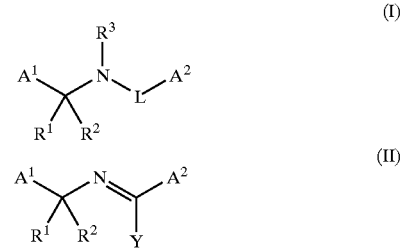

wherein

A$^1$ is a 2-pyridyl or its N-oxide, each of which may be substituted by up to four groups at least one of which is haloalkyl;

A$^2$ is heterocyclyl or carbocyclyl, each of which may be substituted;

R$^1$ and R$^2$, which may be the same or different, are R$^b$, cyano, nitro, halogen, —OR$^b$, —SR$^b$ or optionally substituted amino, or R$^1$ or R$^2$ together with the carbon to which they are attached may form a 3-, 4-, 5- or 6-, carbo- or heterocyclic ring, which may be substituted;

R$^3$ is R$^b$, —OR$^b$, or —N(R$^b$)$_2$, cyano, N-substituted iminomethyl or nitro; or R$^3$ and A$^2$, together with the interconnecting atoms, may for a 5- or 6-membered ring;

L is —C(=X)— or —SO$_2$—, where X is oxygen, sulfur, N—OR$^b$, N—R$^b$ or N—N(R$^b$)$_2$; and Y is halogen, —OR$^b$, —SR$^b$, —N(R$^b$)$_2$, —NR$^b$(OR$^b$) or —NR$^b$N(R$^b$)$_2$; and R$^b$, which may be the same or different is alkyl, alkenyl, alkynyl, carbocyclyl or heterocyclyl, each of which may be substituted; or hydrogen or acyl, or two adjacent R$^b$ groups together with the interconnecting atoms, may form a 5- or 6-membered ring;

with the proviso that when A$^1$ is 2-pyridyl, R$^1$ is hydrogen, R$^2$ is hydrogen, optionally substituted alkyl or acyl, L is —C(=X)— or —SO$_2$—, X is oxygen or sulfur and R$^3$ is hydrogen or optionally substituted alkyl, A$^2$ is not optionally substituted phenyl.

* * * * *